United States Patent
Inam et al.

(10) Patent No.: US 12,159,376 B2
(45) Date of Patent: Dec. 3, 2024

(54) AUTOMATIC REDUCTION OF THE APPEARANCE OF MACH BAND EFFECT ON RADIOGRAPHS

(71) Applicant: OverJet, Inc., Boston, MA (US)

(72) Inventors: Wardah Inam, Cambridge, MA (US); Jack C. Kwok, Walnut Creek, CA (US); Samet Taspinar, Watertown, MA (US)

(73) Assignee: OverJet, Inc., Boston, MA (US)

( * ) Notice: Subject to any disclaimer, the term of this patent is extended or adjusted under 35 U.S.C. 154(b) by 394 days.

(21) Appl. No.: 17/559,638

(22) Filed: Dec. 22, 2021

(65) Prior Publication Data

US 2022/0198613 A1    Jun. 23, 2022

Related U.S. Application Data

(60) Provisional application No. 63/128,879, filed on Dec. 22, 2020.

(51) Int. Cl.
*G06K 9/00* (2022.01)
*G06N 3/08* (2023.01)
*G06T 5/70* (2024.01)
*G16H 30/40* (2018.01)

(52) U.S. Cl.
CPC .............. *G06T 5/70* (2024.01); *G06N 3/08* (2013.01); *G16H 30/40* (2018.01); *G06T 2207/10116* (2013.01); *G06T 2207/20081* (2013.01); *G06T 2207/20084* (2013.01); *G06T 2207/30036* (2013.01)

(58) Field of Classification Search
CPC . G06T 2207/10081; G06T 2207/10104; G06T 2207/10108; G06T 2207/10112; G06T 2207/10116; G06T 2207/10121; G06T 2207/10124; G06T 2207/10128; G06T 2207/30036; A61B 5/4547; A61B 6/51; G16H 30/40; G16H 50/20; G16H 70/20
See application file for complete search history.

(56) References Cited

U.S. PATENT DOCUMENTS

| | | | |
|---|---|---|---|
| 2006/0072799 A1* | 4/2006 | McLain | G06T 11/206 382/128 |
| 2021/0357688 A1* | 11/2021 | Kearney | G06F 18/214 |
| 2022/0180527 A1* | 6/2022 | Hagi | G06T 7/11 |

FOREIGN PATENT DOCUMENTS

| | | | | |
|---|---|---|---|---|
| KR | 20180045551 A | * | 5/2018 | ............. G06N 99/00 |
| KR | 102072052 B1 | * | 1/2020 | ............. G06T 7/187 |

* cited by examiner

*Primary Examiner* — Atiba O Fitzpatrick
(74) *Attorney, Agent, or Firm* — Sunstein LLP (57) ABSTRACT

Disclosed techniques include radiograph analysis based on Mach band effects. A dental radiographic image is obtained. A high contrast structure on the image is detected. The high contrast structure comprises a radiopaque structure. The structure is analyzed to identify a dental restoration. Contrast is evaluated for the presence of Mach band effects from the dental restoration. A boundary for the dental restoration is determined based on the analyzing and the evaluating. The image is colorized to display the dental restoration based on the boundary that was determined wherein the color for the dental restoration is represented as a darker color than originally on the image.

21 Claims, 7 Drawing Sheets

AUTOMATIC REDUCTION OF THE APPEARANCE OF MACH BAND EFFECT ON RADIOGRAPHS

This application claims priority to provisional application 63/128,879, filed Dec. 22, 2020, which is herein incorporated by reference in its entirety.

TECHNICAL FIELD

This application relates generally to analysis and more particularly to automatic reduction of the appearance of Mach band effect on radiographs.

BACKGROUND ART

Regular dental office visits enable dentists to diagnose and treat dental disease in its earliest stages. Dentists can identify dental caries (for example, cavities), which are small holes that form due to tooth decay. Cavities form in places such as in grooves, between teeth, and at the margins of dental work. When cavities are identified, a dentist will remove all the tooth decay and then fill the cavity with a restoration (for example, a filling), which can be made of materials such as composites, gold, and ceramics. To find problems which cannot be seen through a visual examination, dentists use radiographs (for example, x-rays). In dental x-rays, grayscale images of teeth, bone, and the tissues around them are examined. Cavities are seen as radiolucent (e.g., dark areas and the like) on teeth. X-rays can show dark areas which are not cavities but are related to an optical illusion called the Mach band effect. This occurs at the edge of two areas with significant difference in their brightness (e.g., one area can be dark, the other bright and the like). Because restorations (such as filling, crown, root canal treatment or any other restorative operation) are made of dense materials, they appear as high contrast, radiopaque structures (e.g., bright areas and the like) in x-rays. The gray areas of a tooth, like enamel and dentin, can appear darker near the edges of restorations due to the Mach band effect. Such optical illusion can lead to misdiagnosis that the darker appearing areas may be diagnosed as cavities. This may lead to unnecessary dental treatment. Conversely, misdiagnosing a cavity as a Mach band leads to skipping needed treatment.

SUMMARY OF THE EMBODIMENTS

In accordance with one embodiment of the invention, a computer-implemented method for mitigating a Mach band effect in a digitized radiographic image. The method is performed by a computer system executing computer processes comprising:
 using a computer vision system to analyze the image to identify a boundary between two regions associated with a set of physiological features and having a contrast difference sufficient to warrant an inference of presence of the Mach band effect therein; and
 modifying the image to reduce the inferred Mach band effect.

In an optional embodiment, the physiological feature of interest is a dental restoration. Optionally, the computer vision system is configured to differentiate between a dental restoration and a naturally occurring anatomical feature. Also optionally, the computer vision system is a neural network, and as a further option a convolutional neural network or transformer neural network.

Optionally, when using a neural network, said neural network is trained using a plurality of images, a first subset of which includes images of dental restorations. Further optionally, the neural network is trained using a second subset of the plurality of images which include images only of naturally occurring anatomical features.

Further optionally, the first subset and second subset are annotated before the neural network is trained.

In an optional embodiment, upon identifying the boundary a delta region is added beyond an edge of the dental restoration shown in the image. Also optionally, using the computer vision system to analyze the image further comprises identifying a decay. Optionally, the identified decay is adjacent to the dental restoration. Further optionally, after the computer vision system analyzes the image to identify decay, calculating a probability metric for cavity existence within the image.

Optionally, the dental restorations comprise a filling. Also optionally, the computer implemented method further comprises causing display of the dental restoration and the naturally occurring anatomical feature in distinctive colors. Further optionally, the display of decay is shown in a distinct color from the dental restoration and the naturally occurring anatomical feature.

Optionally, the color of the dental restoration and the naturally occurring anatomical feature are based on a user selection. Also optionally, the method generates a dental treatment based on the identified decay. Further optionally, the computer vision system is used to analyze the image based on radiolucencies in the image.

Optionally, the radiographic image includes radiographic data. Also optionally, the computer vision system further comprises analyzing further images associated with the image to identify dental restoration and Mach band effects. Optionally, said further images are taken over a period of time.

In accordance with another embodiment of the invention a non-transitory storage medium is provided. The storage medium stores instructions that, when executed, establish computer processes, the computer processes comprising:
 using a computer vision system to analyze the image to identify a boundary between two regions associated with a set of physiological features and having a contrast difference sufficient to warrant an inference of presence of the Mach band effect therein; and
 modifying the image to reduce the inferred Mach band effect.

BRIEF DESCRIPTION OF THE DRAWINGS

The foregoing features of embodiments will be more readily understood by reference to the following detailed description, taken with reference to the accompanying drawings, in which.

The following detailed description of certain embodiments may be understood by reference to the following figures wherein.

DETAILED DESCRIPTION OF SPECIFIC EMBODIMENTS

Definitions. As used in this description and the accompanying claims, the following terms shall have the meanings indicated, unless the context otherwise requires:

A "set" is a group comprising at least one member.

A "computer vision system" is an image processing arrangement that may employ traditional image processing, or convolutional neural network processing, or transformer neural network processing, or any other method of image processing.

A "computer process" is the performance of a described function in a computer system using computer hardware (such as a processor, field-programmable gate array or other electronic combinatorial logic, or similar device), which may be operating under control of software or firmware or a combination of any of these or operating outside control of any of the foregoing. All or part of the described function may be performed by active or passive electronic components, such as transistors or resistors. In using the term "computer process" we do not necessarily require a schedulable entity, or operation of a computer program or a part thereof, although, in some embodiments, a computer process may be implemented by such a schedulable entity, or operation of a computer program or a part thereof. Furthermore, unless the context otherwise requires, a "process" may be implemented using more than one processor or more than one (single- or multi-processor) computer.

A "color in an image" is a visual attribute, in the image, selected from the group consisting of: a grayscale value in a grayscale image and a color value in a color image.

Techniques for radiography analysis based on Mach band effects are disclosed. A dental radiographic image can be obtained. A high contrast structure on the image can be detected. The high contrast structure comprises a radiopaque structure. The structure can be analyzed to identify a dental restoration. The dental restoration comprises a filling. The analysis differentiates between dental restorations and naturally occurring anatomical features. This analysis can be accomplished by using traditional computer vision methods or deep neural networks. First, restorations from an image are extracted using aforementioned methods. Then, areas near the restorations can be analyzed for potential Mach band effects. Based on the analyzing the restorative structures, a boundary for the dental restorations are determined and filled with a darker color. Determining the boundary comprises adding a delta region beyond an edge of the dental restoration shown in the image. The dental restoration can be shown as a first color. Anatomical tissue is shown as a second color. Decay is shown as a third color. The analyzing comprises identifying decay.

Various features, aspects, and advantages of various embodiments will become more apparent from the following further description.

In the disclosed materials, understanding Mach band effects and their impact on radiographs helps in the analysis of x-rays. The radiographs can include dental x-rays. Mach band effects are optical illusions that can enhance the contrast at the borders or edges of slightly differing shades of gray that are in contact with each other. The optical illusion causes the darker shade of gray to appear lighter at the edge, while the lighter shade of gray appears darker at the edge. In the context of observing dental radiographic images, the Mach band effects can cause a human to distort the border of dental restorations, such as a fillings, crowns, and bridges, and the adjacent naturally occurring anatomical features associated with a tooth.

Due to the Mach band effects, a decay can appear as an optical illusion. A practitioner can determine whether decay is present by seeking abnormal variances in density within the tooth, however, the Mach band effects can lead a practitioner to conclude a false positive for decay. The false positive results from difficulty in distinguishing a Mach band effect from actual decay. The clear determination of the boundary between the dental restoration and the tooth is necessary to determine the presence or absence of decay adjacent to the dental restoration. The disclosed techniques can be used for other anatomical portions beyond mouth and dental regions. X-rays of various joints and body portions can be similarly analyzed. Resulting radiographs can be colorized. Colors can be changed for plates, pins, artificial joints, and other devices inserted into a body.

Proposed techniques include adding a delta region to the border to extend it slightly beyond the edge of the dental restoration. The delta region is an incremental expansion of the region associated with the dental restoration. The delta region, therefore, expands the border between the dental restoration and the tooth. The expansion can be accomplished by adding a set of pixels around the area of the restoration. In some embodiments, the expansion can be accomplished by growing the restoration area by fixed distance or a fixed percentage.

In one embodiment, a dental restoration can be colorized to have the restoration displayed with a darker color than originally included in the image. The darker color can be grayscale or it can be a color such as dark brown, dark blue, or some other color.

In one embodiment, the restoration replacement color is calculated as the average color of the immediate surrounding tooth area. The average color of an area is the sum of each RGB value across all pixels within the area divided by the number of pixels in the area. The tooth area is determined by a tooth instance segmentation neural network algorithm using modeling in a manner analogous to the model described above in connection with tooth decay. Such a neural network may, for example, be a convolutional neural network (CNN) or a transformer neural network. In some embodiments, the tooth area is determined by other methods, such as computer vision (CV). The immediate surrounding tooth area is the subset of the tooth pixels located within a short distance from the restoration area.

In a similar embodiment, instead of replacing the entire restoration area with a solid color, the brightness of the restoration area is automatically reduced to more closely match the average brightness of its immediate surrounding tooth area. The benefit over single color replacement is that any texture is preserved.

In one embodiment, an adjustment knob is used to allow the operator to manually decrease the brightness of a restoration area. The knob can be a software graphical interface or a hardware input device. The knob allows the operator to tune, in small increments, the brightness level of a restoration area to reduce the Mach band effect. The operator can perform a reset to restore the restoration area to its original brightness.

The modified dental restoration can reduce any optical illusion caused by Mach bands around the restoration. Color adjustment can be performed automatically using standard colors or using user selected colors. A plurality of colors can be used to highlight critical aspects of the dental radiographic image including the dental restoration, anatomical tissue, the border between the dental restoration and the tissue, decay, and so on. In various embodiments, features such as analyzing the structure to identify a dental restoration, evaluating contrast for presence of Mach band effects from the dental restoration, determining the boundary of the dental restoration, and colorization of the dental restoration are accomplished using deep learning or traditional computer vision methods.

In one embodiment, a dental radiographic image is obtained from an individual. The radiographic image can include a high contrast structure, where the high contrast structure can include a dental restoration. Radiographic data is obtained using ionizing and nonionizing radiographic techniques. The obtaining can include obtaining further radiographic images of the individual. A high contrast or radiopaque structure is detected on the image. The high contrast structure can include a shape, a point, a curve, and so on. The high contrast structure can be partially or fully included within the image. The structure that was detected can be analyzed to identify a dental restoration. The dental restoration can include a filling, a crown, a bridge, an implant, or other dental restoration. Mach band effects from the dental restoration can be evaluated. The Mach bands, which can be perceived in the region of a boundary, particularly at an abrupt change, may be present within the dental radiographic image. A boundary is determined for the dental restoration based on analyzing the structure and evaluating the contrast for potential Mach band effects.

Figure 1:
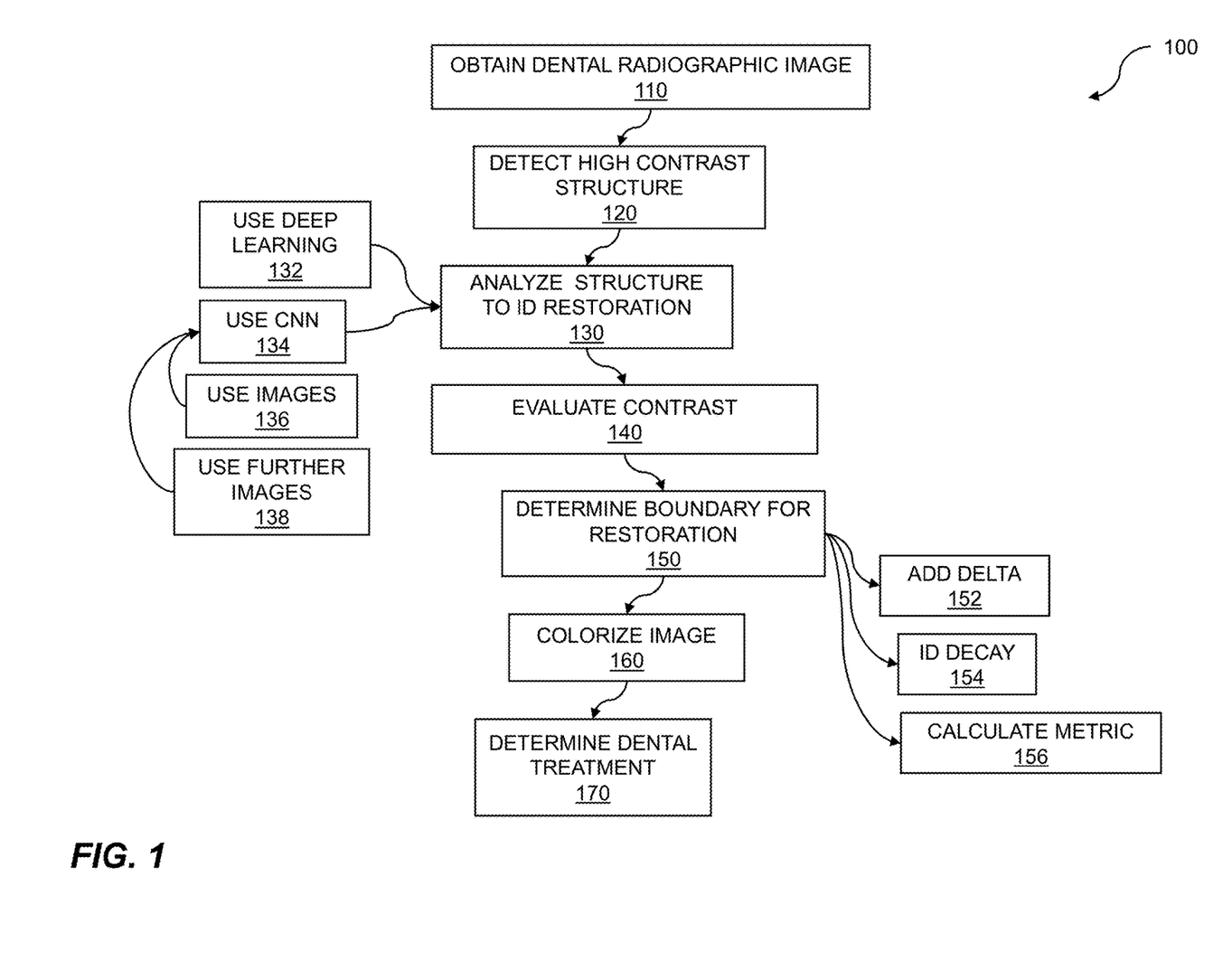
FIG. 1 is a flow diagram of processes for radiograph analysis based on Mach band effects in accordance with one embodiment of the invention.

FIG. 1 is a flow diagram of processes for radiograph analysis based on Mach band effects in accordance with one embodiment of the invention. The flow diagram 100 is based on a computer-implemented method for analysis, wherein the analysis can be performed on dental radiographic images. The analysis is based on Mach band effects. The flow diagram 100 includes obtaining, at step 110, a dental radiographic image, such as shown in 410 in FIG. 4, discussed below. In various embodiments, the radiographic image is based on ionizing and nonionizing radiation. In some embodiments, the dental radiographic image includes a dental x-ray image. The dental radiographic image can be uploaded by a user, obtained from a repository of radiographic images such as a HIPAA compliant repository, downloaded over a computer network, and so on. In some embodiments, the image includes radiographic data. The flow diagram 100 includes detecting, at step 120, a high contrast structure on the image based on one or more processing techniques, such as image processing techniques. Image processing techniques include edge detection, pixel value variations or ranges, and so on. The high contrast structure can include an anatomical tissue feature such as tooth, bone, dental restoration, implant, or appliance, and the like. In some embodiments, the high contrast structure includes a radiopaque structure.

The flow diagram 100 includes analyzing, at step 130, the structure to identify a dental restoration based on various attributes in the image such as density of the high-density structure, shape of the structure, location of the structure within the image, and so on. Analyzing the structure differentiates between dental restorations and naturally occurring anatomical features. Dental restorations include fillings, crowns, implants, appliances such as bridges, and the like. Analyzing, in step 130, is based on radiolucencies in the image. In one embodiment, the analyzing in step 132 is accomplished using computer vision algorithms. Computer vision gives computers have a high level understanding of videos or images. These methods exclude deep learning methods. In Computer vision methods, algorithms with fixed or adaptive parameters help accomplish a task such as finding edges in an image, or fixing objects within images. Moreover, these methods are incorporated with deep learning methods such as fine-tuning the results of deep learning models using some image statistics. These algorithms may or may not require a training step prior to analysis purpose.

In the flow diagram 100, analyzing is performed, in step 134, using a convolutional neural network (CNN). In other embodiments, the same process is performed using different forms of computer vision, such as transformer neural networks. The embodiment of flow diagram 100 uses a CNN, which is a configuration of a neural network that is well suited to image analysis applications. The CNN includes a plurality of layers, where a subset of the layers can include feature learning layers, and a second subset of the layers include classification layers. The layers within the CNN can include one or more of: a convolution layer, a rectifier linear unit (ReLU) layer, a pooling layer, a batch normalization layer, a flattening layer, a fully connected layer, a softmax layer, etc. The CNN is used to detect restoration instances and can create a segmentation mask which assigns a value to each pixel. This way, each restoration can be a separate object.

In flow diagram 100, the CNN is trained, at step 136, using a plurality of images, a subset of which includes dental restorations. Training of a neural network, a deep learning network, a CNN, etc. is accomplished by providing a training dataset which includes images and annotation results based on those images. In some embodiments, the annotations are polygons delineating the restoration areas. The results may include that a dental restoration is present within an image known to include a dental restoration. Other results can include that no dental restoration is present within an image known to not include a dental restoration. By applying a sufficiently large, typically having one thousand to a hundred thousand images, training dataset to the CNN, the CNN "learns" to identify which images include a dental restoration and which images do not. In one embodiment, the CNN learns to identify precise restoration areas at the pixel level. It solves a problem known as instance segmentation where each restoration area within an image is an "instance." The accuracy of the CNN is improved by applying more training datasets to the training of the CNN. In flow diagram 100, the CNN is trained, at step 138, using a further subset of the plurality of images that include only naturally occurring anatomical features.

In some embodiments, the CNN or other computer vision (CV) detect decays on radiographic images that are darker regions compared to restorations. The CNN and CV algorithms can be trained to segment out or create bounding boxes around decays. In other embodiments, a combination of CNN and CV algorithms is used to detect decays. In some embodiments, CNN and CV algorithms are used to detect other dental diseases or anomalies on radiographic images such as wear, erosion, broken teeth, remaining pieces of broken teeth and so on. These diseases or anomalies have similar structures as decays where they are typically darker compared to restorations.

In some embodiments, the CNN and CV algorithms can help detect decays and other diseases around restorations such that they would help annotators such as hygienists or dentists to eliminate potential false negatives (for example, a dentist may think a decay is actually because of Mach band effect, but the models can help show the object is indeed a decay).

The flow diagram 100 includes evaluating, at step 140, contrast for potential presence of Mach band effects from the dental restoration. Discussed throughout, Mach band effects are optical illusions that can enhance or alter the contrast at the borders or edges of slightly differing shades of gray that are in contact with each other. The results of the optical illusion are that the darker shade of gray appears, to a human, lighter at the edge, while the lighter shade of gray appears darker at the edge. Flow diagram 100 includes determining a boundary 150 for the dental restoration based on analyzing the structure and evaluating the Mach band effects. The boundary is between the radio opaque high contrast structure and one or more naturally occurring anatomical structures. The boundary may include a point, a line, a curve, etc. In some embodiments, determining the boundary 150 is further based on images and analyzing and evaluating the further images for dental restorations and Mach band effects. The further images include further dental radiographic images, where the further images can be obtained at substantially the same time as obtaining the image. In other embodiments, determining the boundary is based on a set of images taken over a period of time. In flow diagram 100, determining the boundary includes adding a delta region 152 beyond an edge of the dental restoration shown in the image. Adding the delta region to a boundary is used to reduce Mach band effects. The flow diagram 100 further includes identifying possible decay 154. Identifying possible decay can be based on evaluating the dental restoration for potential Mach band effects. Detection of decay adjacent to the border of the dental restoration can be difficult to detect to the Mach band effects. Flow diagram 100 includes calculating a probability metric for cavity existence within the image. The metric can be based on a value, a range of values, a percentage, a probability, a text result such as "Likely" or "Not likely," etc.

Flow diagram 100 includes colorizing the image 160 to display the dental restoration, which reduces Mach band effects. In one embodiment, the dental restoration can be colorized a first color using a variety of techniques. In various embodiments, colorizing is performed based on a user selection, the user selects a color from a pulldown menu, from a color wheel or chart, and the like. In other embodiments, colorizing can be accomplished automatically, based on defaults, industry standard color conventions, etc. In some embodiments, the image and the first color comprise a grayscale monochromatic image. The first color can further include a grayscale selection, a fill pattern, etc. In some embodiments, the first color is black. Other features within the dental radiographic image can be colorized. In some embodiments, anatomical tissue can be shown as a second color, a second grayscale selection, a second fill pattern, and the like. Further colors can be used for additional anatomical tissue types such a tooth, gum, jaw, and so on. In some embodiments, decay can be shown as a third color. The decay can also be shown as a third grayscale selection, a third pattern, etc. The colorizing the decay can enhance viewing of the decay. The flow diagram 100 further includes determining a dental treatment 170 based on the analyzing the structure and the determining the boundary for the dental restoration and the colorizing the restoration to reduce Mach band effects. The treatment can include replacement of the dental restoration such as refilling dental caries, replacing or providing a dental restoration such as a crown, providing a dental restoration such as a bridge, and the like. Various steps in the flow diagram 100 may be changed in order, repeated, omitted, or the like without departing from the disclosed concepts. Various embodiments of the flow diagram 100 can be included in a computer program product embodied in a non-transitory computer readable medium that includes code executable by one or more processors.

Figure 2:
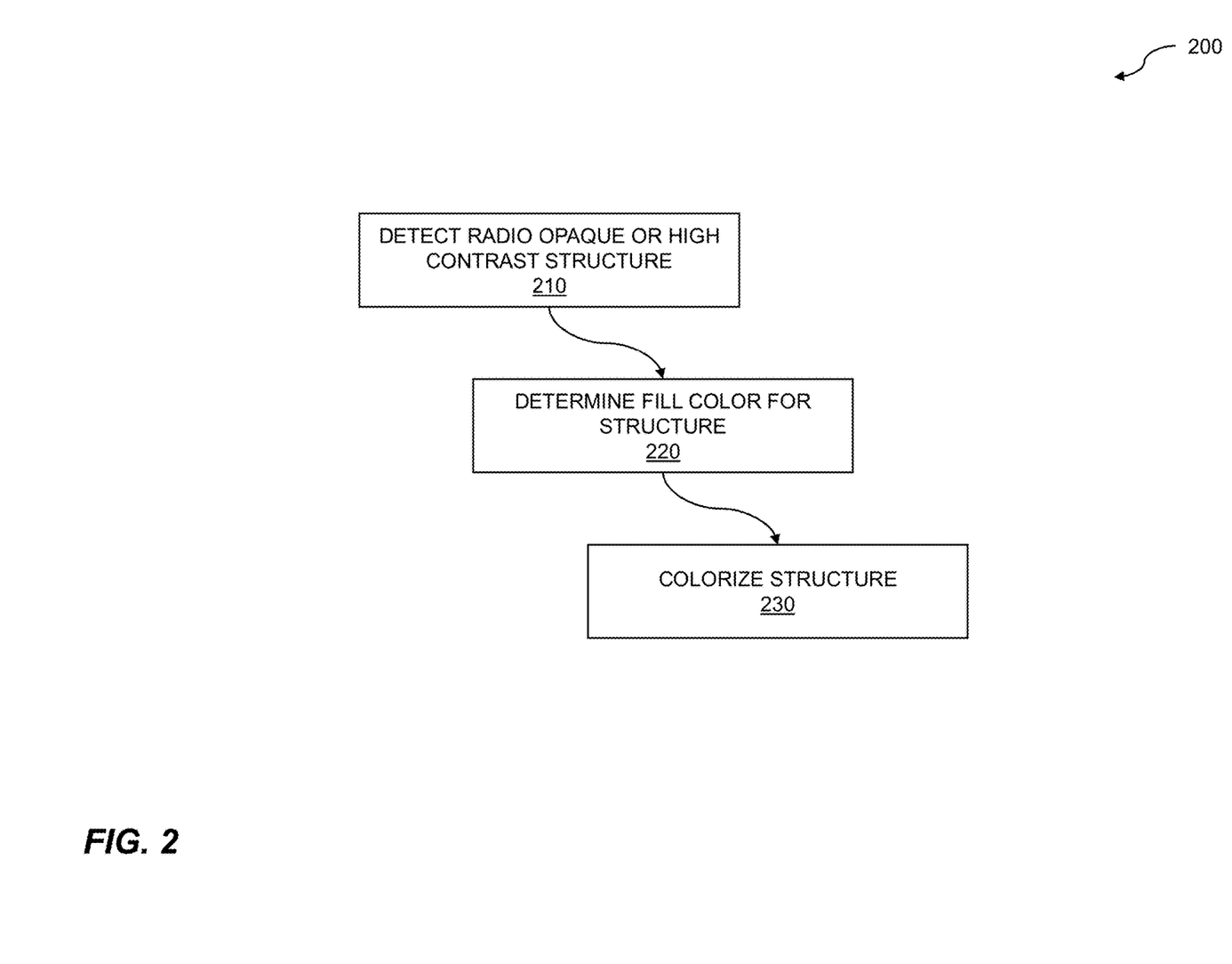
FIG. 2 is a flow diagram of processes for structure colorization in accordance with one embodiment of the invention.

FIG. 2 is a flow diagram of processes for structure colorization in accordance with one embodiment of the invention. A dental radiographic image can be obtained for analysis including analyzing a high contrast structure detected within the image and identifying a dental restoration. The dental restoration can include a filling, a crown, an implant, a bridge, an appliance, and so on. In order to aid a user, such as a practitioner, to find decay or other dental conditions that need to be addressed, structures, objects, regions, and so on, within the image can be colorized. Such colorizing enables radiograph analysis based on Mach band effects. The structure is analyzed to identify a dental restoration and the contrast is evaluated for the potential of Mach band effects. A boundary for the dental restoration is determined based on the analyzing the structure and the evaluating the Mach band effects. The dental restoration is colorized based on the determined boundary.

The flow diagram 200 includes detecting 210 a radiopaque or high contrast structure on a radiographic image. In one embodiment, the radiographic image is an x-ray image. In radiographic images, radiopaque structure blocks or reduces transmission of an electromagnetic or radio source. The radio opaque structure can show up in negative within an image such as a dental radiographic image. Flow diagram 200 includes determining a boundary for the dental restoration based on the analyzing and the evaluating. Flow diagram 200 includes determining a color or fill pattern 220 for the radiopaque or high contrast structure, such as black and white, a grayscale, a range of colors, and so on. The fill pattern can include lines, dots, dashes, zigzags, natural patterns, etc. In different embodiments the color is selected automatically, based on a user selection, and the like. The user can select a color from a digital color wheel, a pulldown menu, etc. The fill patterns can include a color selection for the background and the fill patterns. In some embodiments, the color can be black. Flow diagram 200 includes colorizing the structure 230, which includes filling the structure with a color, a fill pattern, and the like. Various steps in the flow diagram 200 may be changed in order, repeated, omitted, or the like without departing from the disclosed concepts. Various embodiments of the flow diagram 200 can be included in a computer program product embodied in a non-transitory computer readable medium that includes code executable by one or more processors.

Figure 3:
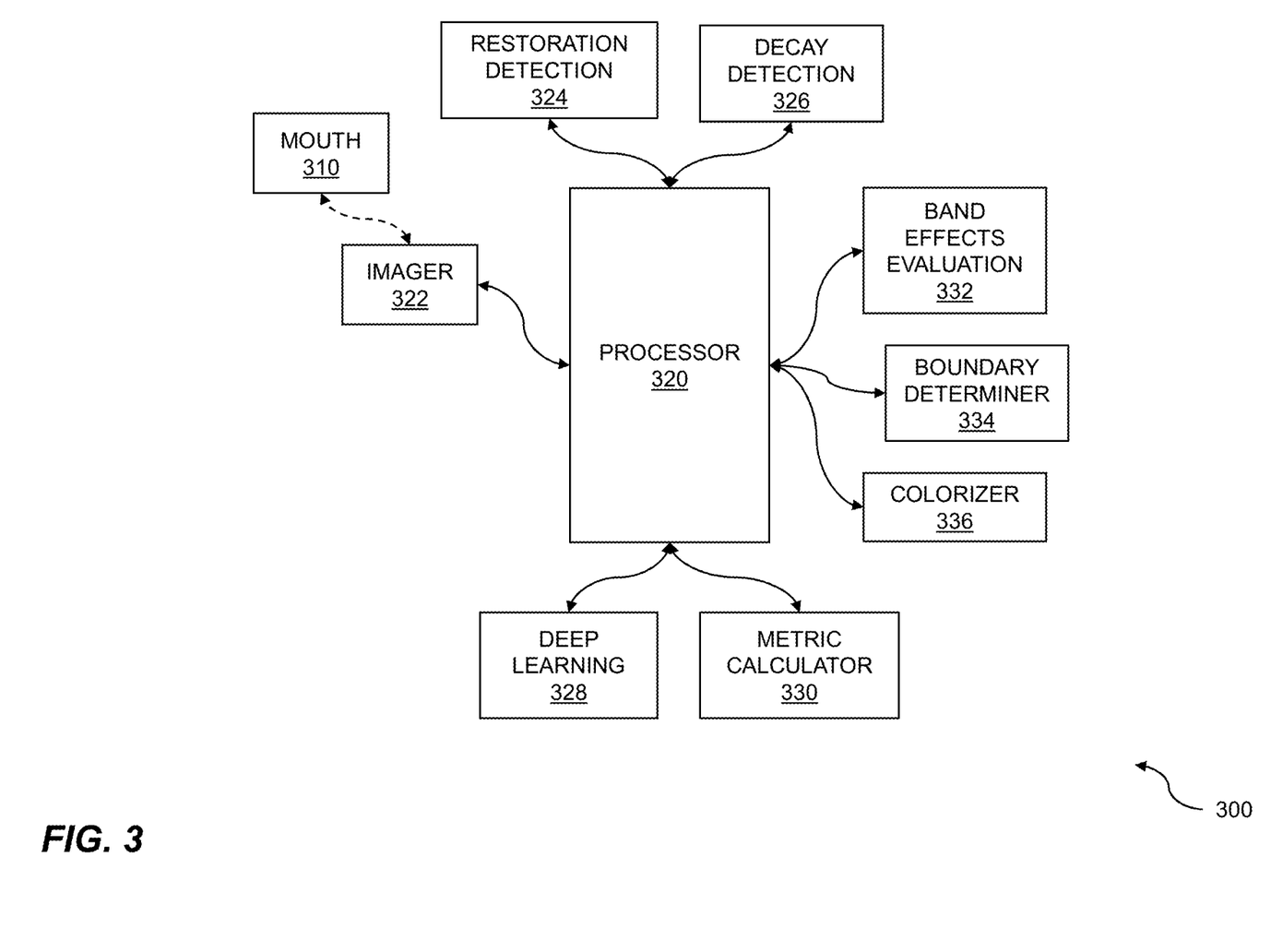
FIG. 3 is a block diagram representation of a system for high contrast structure analysis in accordance with an embodiment of the invention.

FIG. 3 is a block diagram representation of a system for high contrast structure analysis in accordance with an embodiment of the invention. Dental radiographic images, such as x-ray dental images, include data associated with naturally occurring anatomical features, dental restorations, and so on. When present, high contrast structures in an image are analyzed to determine the presence of dental restorations, potential decay, and so on. High contrast structure analysis enables radiograph analysis with reduced Mach band effects. If a high contrast structure is detected on the image, the structure is analyzed to identify a dental restoration and the contrast is evaluated for potential Mach band effects. A boundary of the dental restoration is determined based on analyzing the restorative structure and evaluating the contrast for potential Mach band effects. The dental restoration is then colorized based on the boundary to reduce Mach band effects.

Block diagram 300 includes an input from which radiographic data can be obtained, such as a mouth 310. The data can be obtained "live" from an individual during a dental appointment, uploaded by a user, obtained from a repository such as a HIPAA compliant repository, downloaded over a computer network such as the internet, and so on. Block diagram 300 includes processor 320. Processor 320 may comprise a standalone processor, a server, a plurality of processors, processors within integrated circuits or chips, and the like. The processor 320 is used to capture input data. In the embodiment of FIG. 3, processor 320 is coupled to or in communication with imager 322, which is used to capture data associated with the input 310. The imager may include a radiographic imager, where the radiographic imager can be used to capture x-ray images of the mouth. The processor 320 is coupled to a restoration detection component 324, which is used to detect dental restoration such as a filling, a crown, an implant, a bridge, etc. The processor 320 is also coupled to decay detection component 326, which detects decay in untreated teeth, decay in a tooth that was previously treated, and so on. In some embodiments, detecting decay includes decay that is adjacent to the detected dental restoration.

In block diagram 300 processor 320 is coupled to a deep learning component 328. The deep learning component can be used for analysis of a high contrast structure within the dental radiographic image. In some embodiments, analyzing based on deep learning is performed using a convolutional neural network or a transformer neural network. In one embodiment, the neural network is trained using image data prior to application of deep learning to the analysis. Processor 320 is coupled to a metric calculator 330. The metric calculator can be used to calculate a probability metric for cavity existence within the image. The probability metric can be based on a text evaluation such as high, medium, or low probability; on a percenter; on a value, and so on. The processor is coupled to a band effects evaluation component 332. The Mach band effects can appear as optical illusions and can obscure the presence or absence of decay at a boundary of a dental restoration. The processor 320 is coupled to a boundary determiner 334, which determines a boundary based on image processing techniques such as edge detection. In some embodiments, determining the boundary includes adding a delta region beyond an edge of the dental restoration shown in the image.

The processor 320 is coupled to a colorizer 336. The colorizer 336 adds synthetic or "false" color to the dental radiographic image and reduces Mach band effects. In one embodiment, the colorizer 336 colorizes the image to display the dental restoration and naturally occurring anatomical features. The dental restoration can include a filling, crown, implant, etc. The anatomical tissue can include a tooth, a gum, a jaw, etc. In some embodiments, the dental restoration and a naturally occurring anatomical feature are displayed in distinct colors. The color of the restoration or feature can be determined by a user selecting the color. In various embodiments, additional colors are used to highlight, outline, differentiate, or otherwise denote other features, objects, and so on, within the image. In some embodiments, decay is shown as a color distinct from the anatomical feature and restoration. One or more colors used for colorizing the dental radiographic image can be selected based on a variety of techniques. In some embodiments, the colorizing is performed based on a user selection such as from a pulldown menu, color wheel such as a digital color wheel, and the like. In further embodiments, the colorizing is accomplished automatically, based on default colors, preset colors, standard colors, etc. The colors that can be assigned to the dental restoration, decay, anatomical features, can be changed, modified, altered, and so on. In one embodiment, the colors are inverted within the colorizing. In some embodiments the different colors may be different shades of gray in a grayscale image. In other embodiments, each color may be a different color in a color image.

Figure 4A:
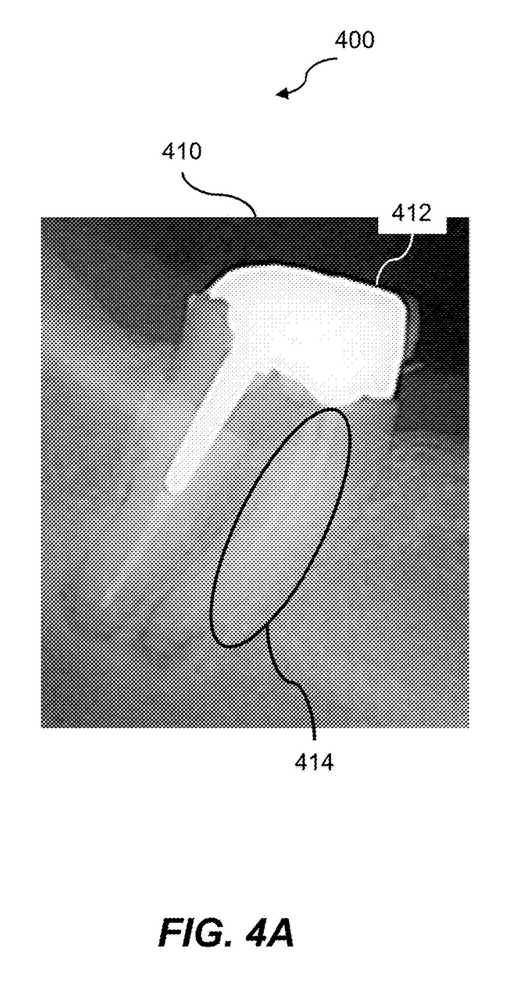
FIGS. 4A and 4B are two radiographic images with a boundary taken by the imager 322 of FIG. 3.
Figure 4B:
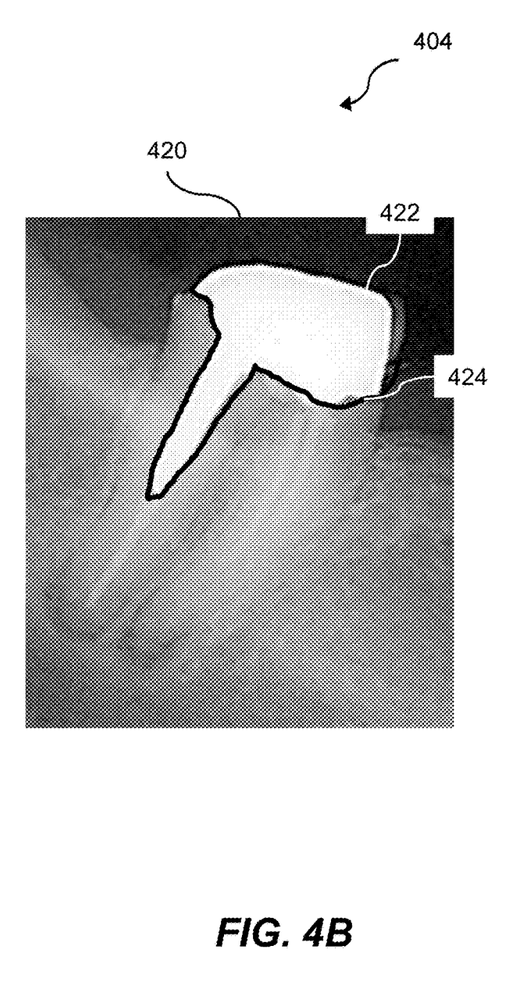

FIGS. 4A and 4B are two radiographic images having a boundary, taken by the imager 322 of FIG. 3. A radiograph image such as a dental radiographic image may include a high contrast structure. The high contrast structure includes a dental restoration such as a crown, a filling, an implant, and so on. A boundary is determined adjacent to a dental restoration. The boundary is used in colorizing a dental restoration to reduce Mach band effects. The colorized radiographic image with boundary is used for radiographic analysis with reduced Mach band effects.

An x-ray image 400 is shown in FIG. 4A. An x-ray image with added boundary 404 is shown in FIG. 4B. An original image 410, such as a radiographic image or x-ray, can include an unaltered or unmanipulated image. The original image can be analyzed to detect a high contrast structure in the image, where the high contrast structure can include a dental restoration such as a filling, a crown, etc. Data associated with the dental restoration is included with x-ray image 400, including patient data. The image shows a high contrast structure, which is a dental restoration 412. In addition to the dental restoration, the image 410 shows further detail 414 of the tooth to which a dental restoration (e.g., root canal treatment) was applied. A second x-ray image 420 is shown, representing an annotated version of the x-ray image 410. The annotated image 420 shows restoration 422 representing restoration 412 in image 410. A boundary 424 has been added to the image 420. The boundary is determined and added to the image using image processing techniques such as edge detection techniques. In one embodiment, determining the boundary includes adding a delta region to expand the boundary by an incremental amount. In some embodiments, a dental treatment is determined based on analyzing the structure and determining the boundary for the dental restoration and colorizing the dental restoration based on the boundary. The dental treatment may include providing a filling, a crown, an implant, no treatment, etc. In other embodiments, determining the boundary can be based on additional images and associated analyzing and evaluating the further images for the dental restoration and Mach band effects.

Figure 4C:
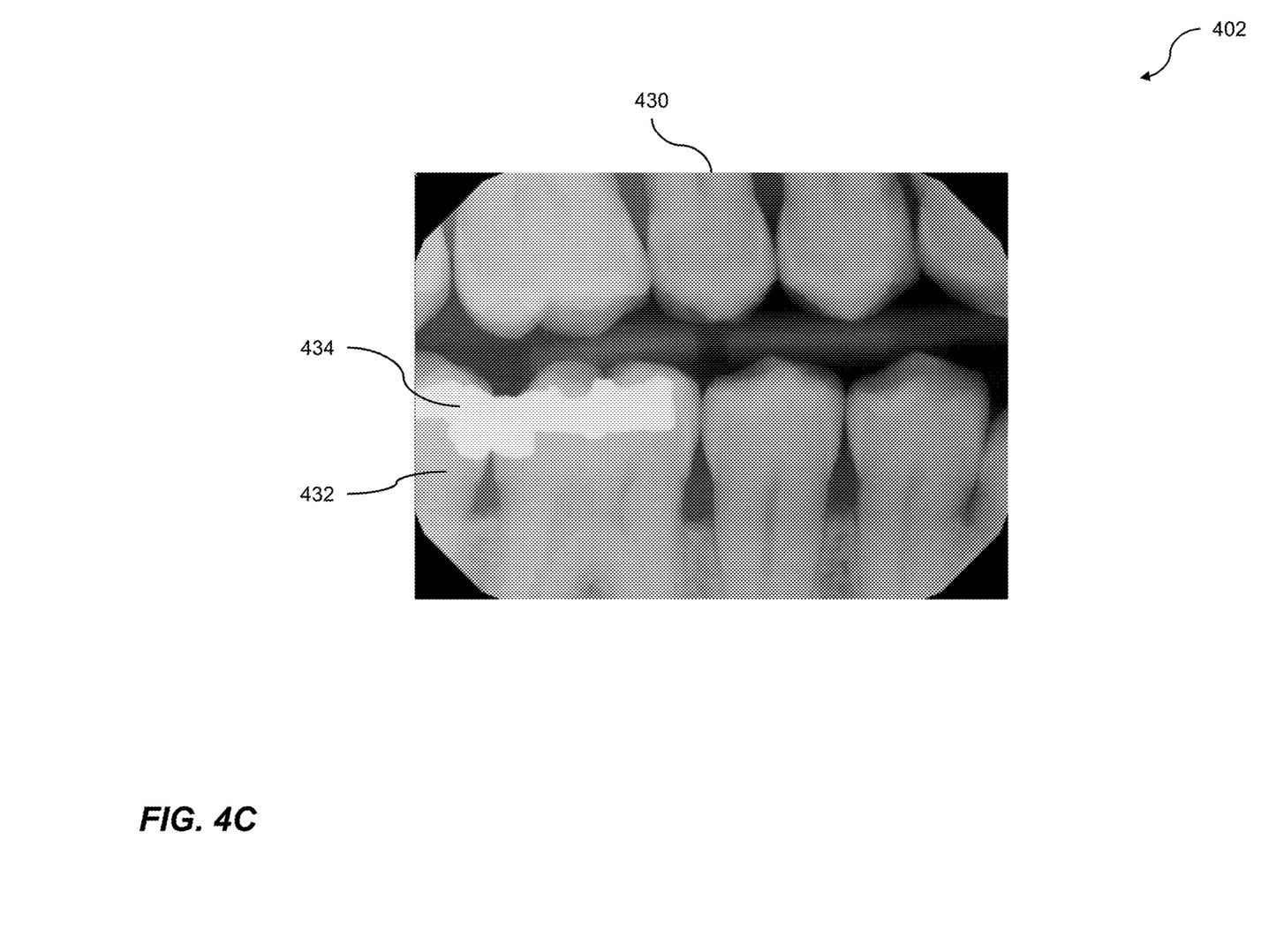
FIG. 4C is a radiographic image with dental restorations 402 taken by the imager 322 in FIG. 3.

FIG. 4C is a radiographic image with dental restorations 402 taken by the imager 322 in FIG. 3. Dental radiographic images such as x-ray images are obtained and analyzed to detect a high contrast structure in the images. The high contrast structure includes a dental restoration such as a filling, a crown, an implant, etc. The radiographic data or image data can include images of an individual prior treatment being performed, after treatment was performed, and so on. Dental radiographic image 430, includes a high contrast structure. The x-ray image 402 is obtained through uploading by a user, downloading from a library of images, obtaining from a repository of images, and so on. The x-ray image 402 is comprised of a bitewing image or other dental x-ray image. Analysis can be performed on the image, wherein analyzing can differentiate between dental restorations and naturally occurring anatomical features. The x-ray image 430 includes naturally occurring anatomical features such as teeth 432, gums, bones, such as jaw bones, etc. The x-ray image 430 further includes a high-density structure 434, where the high-density structure can include a filling. In other embodiments, the high-density structure 434 in the image is associated with other dental restorations such as a crown, an implant, a bridge, and the like.

Figure 5:
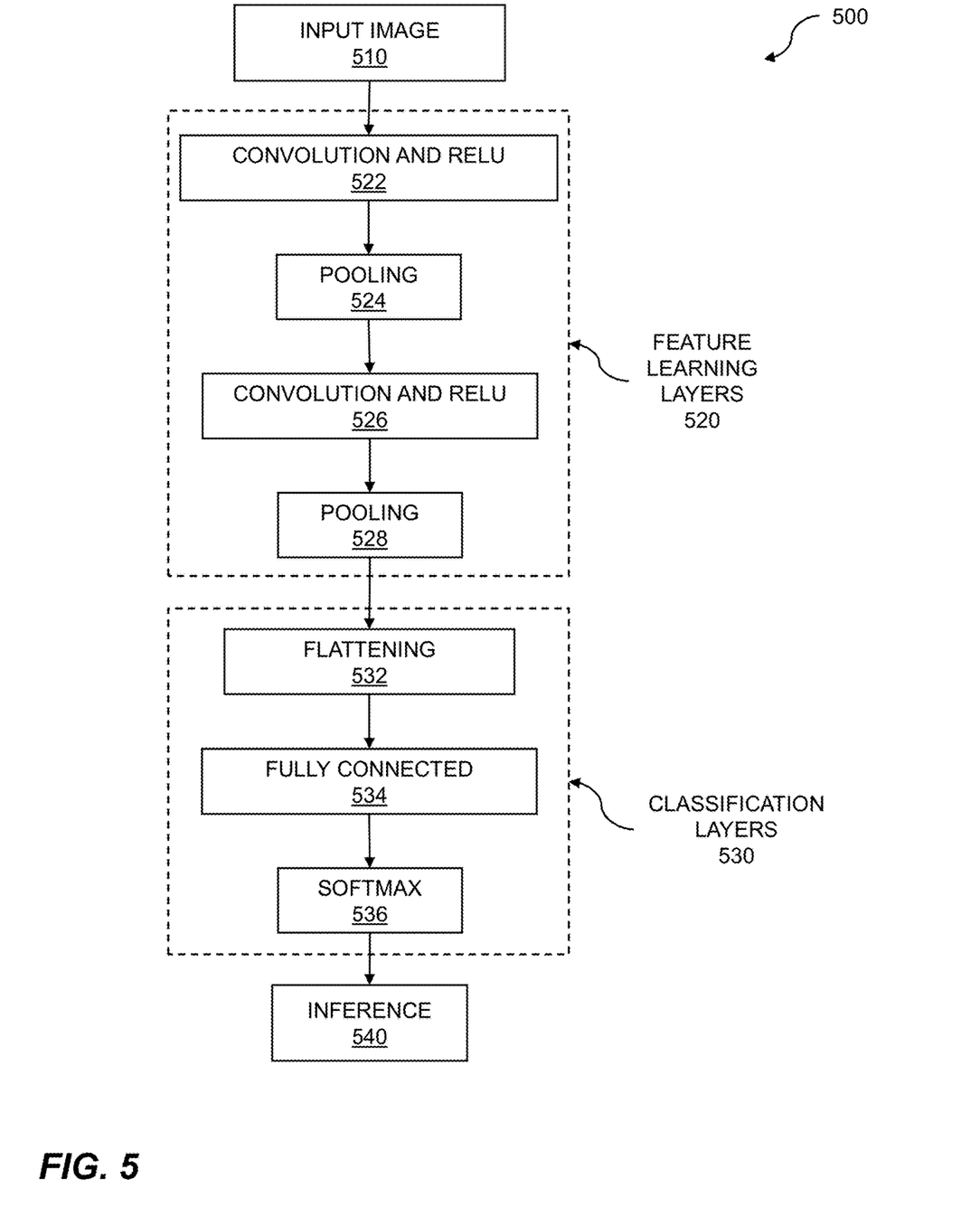
FIG. 5 is a block diagram representation of a neural network in accordance with one embodiment of the invention.

FIG. 5 is a block diagram representation of a neural network in accordance with one embodiment of the invention. In different embodiments, the neural network 500 is a transformer neural network or a convolutional neural network. The neural network includes, inter alia, combinations of one or more inputs, one or more layers, and one or more outputs. The layers comprise one or more nodes, which process data and receive as input, inter alia, a weight and a bias. Data is processed by a given node by applying a weight, a bias, etc., associated with the node, to the processing of the data. Nodes within a layer of a neural network are interconnected with an input, an output of one or more nodes from a prior layer, etc. A neural network enables radiographic analysis with reduced Mach band effects.

Block diagram 500 shows a neural network including a plurality of layers 520, 530, where the layers can perform operations associated with dental radiographic image processing. The neural network 500 receives an input image 510 which is uploaded by a user, obtained from an image repository, downloaded over a computer network such as the internet, and so on. The neural network 500 analyzes the obtained image. Prior to image analysis the neural network requires training. In one embodiment, the neural network is trained using a plurality of images, a subset of which include dental restorations. The images comprise a training dataset and expected results for each image within the training dataset. In some embodiments, the subset is annotated before the neural network is trained. In other embodiments, the neural network is trained using a plurality of images, a subset of which include dental restorations such as crowns, fillings, bridges, implants, etc. In other embodiments, the neural network is trained using a subset of the plurality of images which include only naturally occurring anatomical features. The naturally occurring anatomical features include enamel, dentine, a root, etc., associated with a tooth, bone, gum, etc. In one embodiment, a training dataset includes a plurality of images, which include dental restorations and a plurality of images that do not include dental restorations. The training dataset also includes information that identifies the images that include dental restorations and the images that do not include dental restorations. The neural network is trained by applying the images and examining the predictions or inferences made by the neural network and comparing them to the information associated with the images. The weights and biases associated with the CNN are adjusted as part of the training, to improve the success rate of correctly differentiating images that contain dental restorations and images that do not. Similar methods are used for transformer neural networks The adjusting further speeds convergence by the neural network to its result or inference.

The layers within the neural network 500 include feature learning layers 520. The feature learning layers 520 are used to determine information about the content of the input image 510. The information can include features of the image, where a feature can include an edge or a point, curves or boundaries, an object, and so on. The feature learning layers 520 can include a convolution, transformer, among other things dependent on the type of neural network. The feature learning layer 520 also includes a rectifier linear unit (ReLU) layer 522. The convolution and ReLU perform a convolution operation and a ReLU operation. The ReLU operation comprises an activation operation. The feature learning layers also include pooling layer 524. A pooling operation includes "down sampling" of an image by simplifying further analysis of the image to accomplish local translation invariance within the image. One or more convolution and ReLU layers and one or more pooling layers can be included within the feature learning layers of the neural network. In the example block diagram shown, a second convolution and ReLU layer 526 is included and a second pooling layer 528 is included.

In addition to the feature learning layers, the neural network includes classification layers 530. The classification layers seek to classify an image, where the classification includes identifying an image as including a dental restoration, identifying an image as not including a dental restoration, and so on. The classification layers include flattening layer 532, which takes, as input, an image represented by a 2-D matrix. The 2-D matrix can be converted to a vector. The classification layers include a fully connected layer 534. As the name implies, each node within the connected layer is connected to each node of a previous layer. In the block diagram shown, each node of the fully connected layer is connected to each node of the flattening layer. The classification layers include a softmax layer 536, which is used to normalize a probability distribution function. The softmax layer converts a vector of real values to a vector of real values that sum to 1. Large values in the unconverted vector can receive a high probability while near-zero or negative values can receive a low probability. In one embodiment, the softmax layer can be used as a final activation layer in the neural network. The result of processing the input image by the neural network includes inference 540. The inference, or prediction, can include whether an image includes a dental restoration or not. The inference can further include a presence or absence of decay. The inference can also include a treatment suggestion.

In some embodiments, a combination of CNN and computer vision algorithms work together to determine features such as restorations and decays, as well as the borders where there may potentially be an optical illusion. For example, a CNN model can detect the features and use CV algorithms at the dark regions around the edges so the bright features can be detected. Then another algorithm can tell whether there may be a Mach band effect around the borders. In some embodiments, CV algorithms help improve restoration detection models (the CNN model), in a way to decrease false positives and false negatives.

Figure 6:
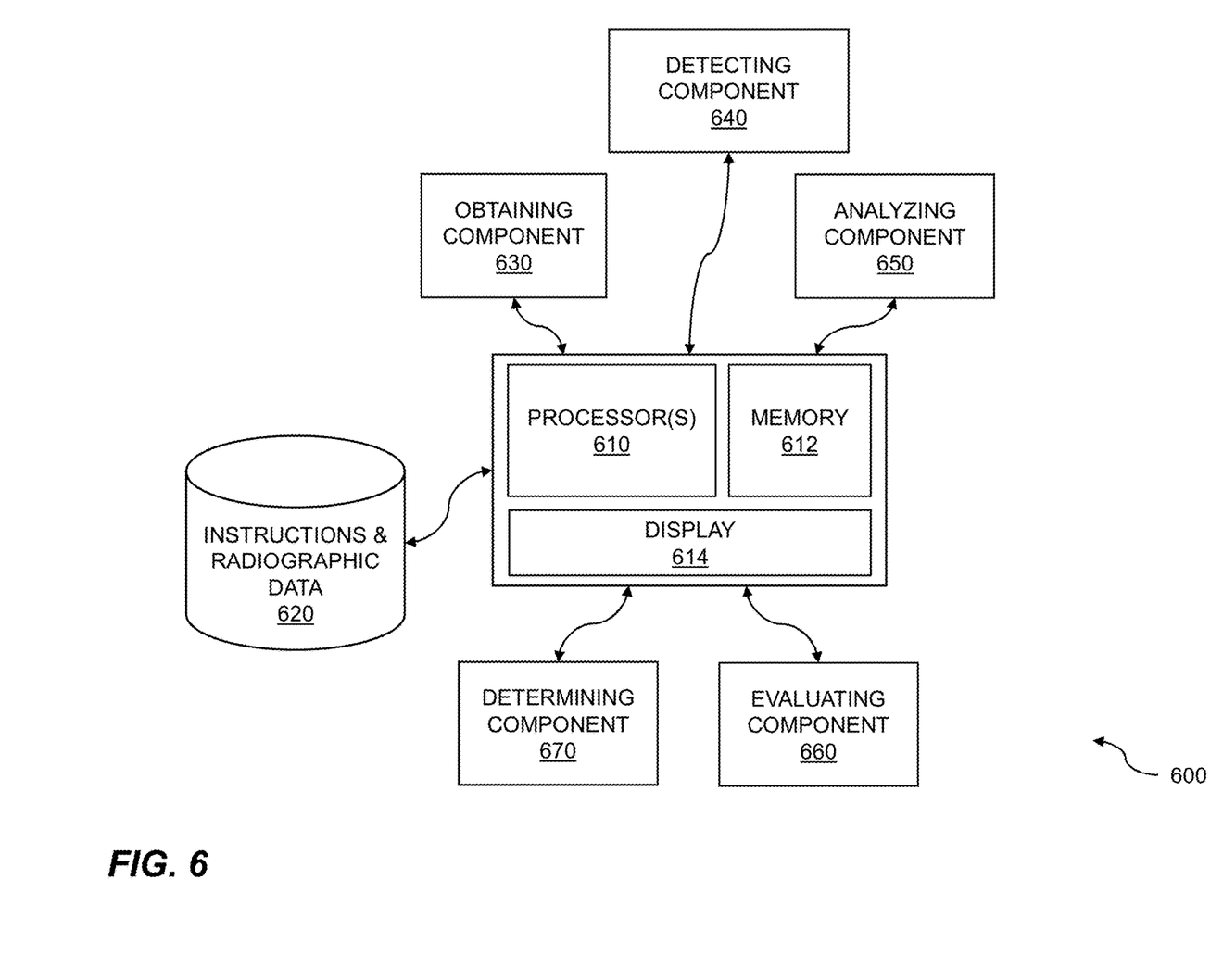
FIG. 6 is a block diagram of a system for radiograph analysis 600, where the radiographic analysis includes reduction of Mach band effects in accordance with an embodiment of the invention.

FIG. 6 is a block diagram of a system for radiograph analysis 600, where the radiographic analysis includes reduction of Mach band effects in accordance with an embodiment of the invention. The system 600 includes a set of processors 610 attached to memory 612, which stores instructions. The system 600 includes a display 614 coupled to the set of processors 610 for displaying data, intermediate steps, instructions, x-ray images, Mach band effect data, and so on. In one embodiment, the memory 612 stores instructions, which when executed by the set of processors 610: obtain a dental radiographic image; detect a high contrast structure on the image; analyze the structure to identify a dental restoration; evaluate contrast for potential Mach band effects; determine a boundary for the dental restoration based on the analyzing the structure and the evaluating the Mach band effects; and colorize the dental restoration based on the boundary that was determined wherein the color for the dental restoration can be represented as a darker color than originally on the image. Analyzing the structure includes identifying decay, wherein the decay can be adjacent to the dental restoration. Detecting decay is aided by determining a boundary for the dental restoration. The radiograph analysis with reduced Mach band effects can be accomplished using processors 610, computers, servers, remote servers, cloud-based servers, and the like.

The system 600 includes a collection of instructions and radiographic data 620. The instructions and radiographic data 620 are stored using an electronic storage coupled to the one or more processors, a database, one or more code libraries, precompiled code segments, source code, apps, or other suitable formats. The instructions include instructions for detecting a high contract structure in an image based on radiographic data analysis. In some embodiments, the radiographic data includes x-ray data. The instructions include instructions for analyzing the structure to identify a dental restoration such as a filling, a crown, and so on. Instructions and radiographic data 620 include instructions for evaluating contrast for presence of Mach band effects from the dental restoration. The Mach band effects include optical illusions seen as bands adjacent to a dental restoration. The instructions 620 further determine a boundary of the dental restoration.

The system 600 includes obtaining component 630. Obtaining component 630 includes functions and instructions for obtaining a dental radiographic image. More than one dental radiographic image is obtained, where the dental images can include various types of radiographic images. The dental radiographic images include x-ray images such as bitewing, periapical, full mouth survey, panoramic, occlusal, and so on. The dental radiographic data is obtainable from a local database, a remote, cloud-based database, a mesh-based database; user uploads; and so on. In optional embodiments, the dental radiographic data is encrypted to meet security and handling requirements such as Health Insurance Portability and Accountability Act (HIPAA) requirements. The dental radiographic data is based on a set of images, a plurality of images taken over a period of time, and the like.

The system 600 includes a detecting component 640. In some embodiments, the detecting component 640 includes functions and instructions for detecting a high contrast structure on the image. In some embodiments, the high contrast structure includes a radiopaque structure. In one embodiment, the radio opaque structure includes an anatomical structure such as a bone, a tooth, and so on. Alternatively, the radio opaque structure includes a dental restoration such as a filling, a crown, and the like. In some embodiments, detecting the high contrast structure is based on edge detection, by a data value of range of data values within the image, etc. The system 600 includes an analyzing component 650, which includes functions and instructions for identifying a dental restoration. Analyzing the structure is based on identifying the structure, locating the structure, and so on. In some embodiments, analyzing differentiates between dental restorations and naturally occurring anatomical features. The dental restorations include a filling, a crown an implant, a bridge, etc. The naturally occurring anatomical features include portions of the tooth such as enamel, dentine, pulp cavity, root, and so on. In some embodiments, the analyzing is accomplished using deep learning. Deep learning is accomplished using a neural network. A neural network for deep learning is trained by providing the neural network with dental images where the correct inferences based on the dental images are known. Some dental images for training in this context include a variety of dental restorations while other images for training are devoid of a restoration. In the course of training for deep learning, the neural network learns to recognize dental restorations and natural features. In other embodiments, the neural network is trained to recognize different features of an image, which may have high contrast differences with the rest of the image. In some embodiments, the analyzing is performed using a neural network such as a transformer neural network or convolutional neural network. The neural network includes a plurality of layers. In various embodiments, the layers within the neural network include one or more of convolution layers, pooling layers, flattening layers, fulling connected layers, softmax layers, etc. In other embodiments, the analyzing can further includes identifying decay. The decay may be adjacent to a dental restoration, remote from the dental restoration, etc. In some embodiments, analyzing is based on radiolucencies in the image.

The system 600 includes an evaluating component 660. In some embodiments, evaluating component 660 includes functions and instructions for evaluating contrast for presence of Mach band effects from the dental restoration. In one embodiment, a Mach band effect includes an artifact within a dental radiographic image, where the artifact can be attributable to human vision, based on luminance detected by a retina. The Mach band can be found adjacent to a curved surface such as a tooth, a dental restoration, and the like. The Mach band effect causes false positives for the presence of decay, masks the presence of decay, and the like.

The system 600 includes a determining component 670. In one embodiment, determining component 670 includes functions and instructions for determining a boundary of the dental restoration based on analyzing the structure and evaluating the Mach band effects. In some embodiments, the boundary is determined based on an edge detection technique. The boundary between a dental restoration and a tooth may not be abruptly delineated within a given dental radiographic image. Therefore, in some embodiments, after determining the boundary, a delta region is added beyond an edge of the dental restoration shown in the image. In other embodiments, determining the boundary is based on analyzing and evaluating additional associated images for dental restoration and Mach band effects. The further images include additional dental radiographic images showing different angles of the dental restoration. In some embodiments, the images include dental radiographic images obtained at substantially the same time. In further embodiments, determining the boundary can be further based on images taken over a period of time. The period of time can include one or more days, weeks, months, or years.

The system 600 includes a computer program product embodied in a non-transitory computer readable medium. In some embodiments, the computer program product comprises code which causes one or more processors to perform operations of: obtaining a dental radiographic image; detecting a high contrast structure on the image; analyzing the structure to identify a dental restoration; evaluating contrast for presence of Mach band effects from the dental restoration; determining a boundary for the dental restoration based on the analyzing the structure and the evaluating the Mach band effects; and colorizing the image to display the dental restoration based on the boundary that was determined wherein the color for the dental restoration can be represented as a darker color than originally on the image.

Each of the above methods may be executed on one or more processors on one or more computer systems. Each of the above methods may be implemented on a semiconductor chip and programmed using special purpose logic, programmable logic, and so on. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or reordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general-purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

Computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, object oriented programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States, then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A computer-implemented method for mitigating a Mach band effect in a digitized radiographic image, the method performed by a computer system executing computer processes comprising:
   using a computer vision system to analyze the image to identify a boundary between two regions associated with a set of physiological features, including a dental restoration and a naturally-occurring anatomical feature, having a contrast difference sufficient to warrant an inference of presence of the Mach band effect therein;
   using the computer vision system produce a distinction between the dental restoration and the naturally occurring anatomical feature; and
   modifying the image, based on the distinction, to reduce the inferred Mach band effect.

2. The method of claim 1, wherein the computer vision system is a neural network.

3. The method of claim 2, wherein the computer vision system is a convolutional neural network.

4. The method of claim 2, wherein the computer vision system is a transformer neural network.

5. The method of claim 2, further comprising training the neural network using a plurality of images, a first subset of which includes images of dental restorations.

6. The method of claim 5, wherein training the neural network further comprises using a second subset of the plurality of images which include images only of naturally occurring anatomical features.

7. The method of claim 6, further comprising, before training the neural network, annotating the first subset and second subset.

8. The method of claim 1, further comprising, upon identifying the boundary, adding a delta region beyond an edge of the dental restoration shown in the image.

9. The method of claim 1, wherein using the computer vision system to analyze the image further includes using the computer vision system to identify a region of decay in the image.

10. The method of claim 9, wherein using the computer vision system to identify the region of decay further includes using the computer vision system to identify the region of decay adjacent to a dental restoration.

11. The method of claim 9, further comprising calculating a probability metric for cavity existence within the image.

12. The method of claim 1, wherein the dental restoration comprises a filling.

13. The method of claim 1, further comprising causing display of the dental restoration and the naturally occurring anatomical feature in distinctive colors.

14. The method of claim 13, wherein causing display of the dental restoration and the naturally occurring anatomical feature includes causing a grayscale display of the dental restoration and naturally occurring anatomical feature.

15. The method of claim 13, further comprising causing display of decay in a first color, the dental restoration in a second color, the naturally occurring anatomical feature in a third color, wherein the first, second, and third colors are mutually distinct.

16. The method of claim 15, further comprising receiving a user selection of the first, second, and third colors and implementing the user selection in causing display.

17. The method of claim 9, further comprising causing display of a dental treatment plan based on the identified region of decay.

18. The method of claim 1, wherein using the computer vision system to analyze the image further comprises analyzing radiolucencies in the image.

19. The method of claim 1, wherein using the computer vision system to identify dental restoration and Mach band effects further includes analyzing a set of additional images corresponding to the image.

20. The method of claim 19, wherein the set of additional images includes an image taken at a first time distinct from a second time at which the digitized radiographic image was taken.

21. A non-transitory storage medium storing instructions that, when executed by a computer, establish computer processes, the computer processes comprising:
using a computer vision system to analyze the image to identify a boundary between two regions associated with a set of physiological features, including a dental restoration and a naturally-occurring anatomical feature, having a contrast difference sufficient to warrant an inference of presence of the Mach band effect therein;
using the computer vision system to produce a distinction between the dental restoration and the naturally occurring anatomical feature; and
modifying the image, based on the distinction, to reduce the inferred Mach band effect.

* * * * *